«12» United States Patent
DeRohan et al.

(10) Patent No.: US 8,849,396 B2
(45) Date of Patent: Sep. 30, 2014

(54) SYSTEMS AND METHODS FOR MAKING AND USING IMPROVED CONNECTOR CONTACTS FOR ELECTRICAL STIMULATION SYSTEMS

(71) Applicant: Boston Scientific Neuromodulation Corporation, Valencia, CA (US)

(72) Inventors: Robert DeRohan, Nipomo, CA (US); Aditya Vasudeo Pandit, Costa Mesa, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 0 days.

(21) Appl. No.: 13/888,923

(22) Filed: May 7, 2013

(65) Prior Publication Data

US 2013/0304140 A1 Nov. 14, 2013

Related U.S. Application Data

(60) Provisional application No. 61/644,323, filed on May 8, 2012.

(51) Int. Cl.
| | |
|---|---|
| *A61N 1/00* | (2006.01) |
| *H01R 24/58* | (2011.01) |
| *H01R 13/24* | (2006.01) |
| *A61N 1/375* | (2006.01) |
| *A61N 1/05* | (2006.01) |
| *H01R 25/00* | (2006.01) |

(52) U.S. Cl.
CPC .............. *A61N 1/05* (2013.01); *H01R 2201/12* (2013.01); *H01R 24/58* (2013.01); *H01R 13/2421* (2013.01); *A61N 1/3752* (2013.01); *A61N 1/0551* (2013.01); *H01R 25/006* (2013.01)
USPC ........................................................... 607/2

(58) Field of Classification Search
USPC ...................................................... 607/2, 37
See application file for complete search history.

(56) References Cited

U.S. PATENT DOCUMENTS

| | | | |
|---|---|---|---|
| 6,181,969 B1 | 1/2001 | Gord | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 7,069,081 B2 * | 6/2006 | Biggs et al. ..................... | 607/37 |
| 7,244,150 B1 | 7/2007 | Brase et al. | |
| 7,437,193 B2 | 10/2008 | Parramon et al. | |
| 7,672,734 B2 | 3/2010 | Anderson et al. | |
| 7,758,384 B2 * | 7/2010 | Alexander et al. ............ | 439/623 |
| 7,761,165 B1 | 7/2010 | He et al. | |

(Continued)

*Primary Examiner* — George Manuel
(74) *Attorney, Agent, or Firm* — Lowe Graham Jones PLLC; Patrick R. Turner (57) ABSTRACT

A port for receiving a lead is defined at a first end of a connector housing of a connector assembly for an implantable electrical medical device. A lumen extends from the port along a longitudinal axis of the connector housing. At least one of a plurality of connector contacts disposed in the connector housing couples to a terminal of the lead when the lead is received by the connector housing. The connector contacts include spring contact probes spaced apart from one another along the longitudinal axis of the connector housing with at least a portion of each of the spring contact probes extending along a first transverse axis into the lumen of the connector housing. The plurality of spring contact probes physically contact the terminals of the lead solely along the first transverse axis when the lead is received by the connector housing.

20 Claims, 8 Drawing Sheets

(56) References Cited

U.S. PATENT DOCUMENTS

| | | |
|---|---|---|
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,364,278 B2 | 1/2013 | Pianca et al. |
| 2007/0150036 A1 | 6/2007 | Anderson |

* cited by examiner

SYSTEMS AND METHODS FOR MAKING AND USING IMPROVED CONNECTOR CONTACTS FOR ELECTRICAL STIMULATION SYSTEMS

CROSS-REFERENCE TO RELATED APPLICATIONS

This application claims the benefit under 35 U.S.C. §119 (e) of U.S. Provisional Patent Application Ser. No. 61/644,323 filed on May 8, 2012, which is incorporated herein by reference.

FIELD

The present invention is directed to the area of implantable electrical stimulation systems and methods of making and using the systems. The present invention is also directed to implantable electrical stimulation systems having connectors with improved connector contacts, as well as methods of making and using the connectors, connector contacts, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat incontinence, as well as a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Conventional implanted electrical stimulation systems are often incompatible with magnetic resonance imaging ("MRI") due to the large radio frequency ("RF") pulses used during MRI. The RF pulses can generate transient signals in the conductors and electrodes of an implanted lead. These signals can have deleterious effects including, for example, unwanted heating of the tissue causing tissue damage, induced currents in the lead, or premature failure of electronic components.

BRIEF SUMMARY

In one embodiment, a connector assembly for an implantable electrical medical device includes an elongated connector housing having a first end, an opposing second end, a longitudinal axis, a first transverse axis transverse to the longitudinal axis, and a second transverse axis transverse to the longitudinal axis and perpendicular to the first transverse axis. A port is defined at the first end of the connector housing. The port is configured and arranged for receiving a proximal end of a lead or lead extension. A lumen is defined in the connector housing and extends from the port along the longitudinal axis of the connector housing. A plurality of connector contacts are disposed in the connector housing. At least one of the plurality of connector contacts is configured and arranged to couple to at least one of a plurality of terminals disposed on the proximal end of the lead or lead extension when the proximal end of the lead or lead extension is received by the connector housing. The plurality of connector contacts include a plurality of spring contact probes spaced apart from one another along the longitudinal axis of the connector housing with at least a portion of each of the plurality of spring contact probes extending along the first transverse axis into the lumen of the connector housing. The plurality of spring contact probes are configured and arranged to physically contact the terminals of the lead or lead extension solely along the first transverse axis when the proximal end of the lead or lead extension is received by the connector housing.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation systems having connectors with improved connector contacts, as well as methods of making and using the connectors, connector contacts, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, deep brain stimulation leads, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,672,734; 7,761,165; 7,949,395; 7,974,706; 8,175,710; 8,224,450; and 8,364,278; and U.S. Patent Application Publication No. 2007/0150036, all of which are incorporated by reference.

Figure 1:
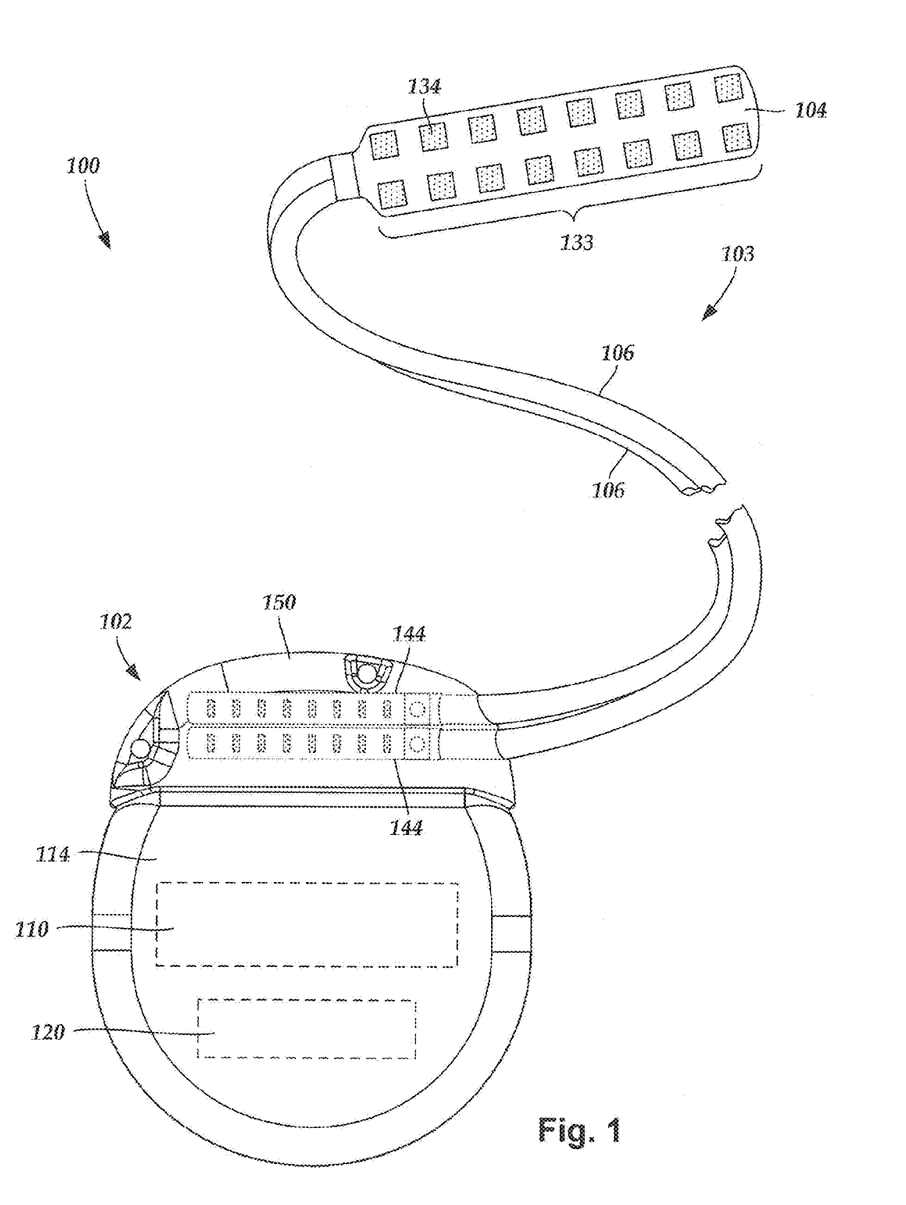
FIG. 1 is a schematic view of one embodiment of an electrical stimulation system that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102 and a lead 103. The lead 103 including a paddle body 104 and one or more lead bodies 106 coupling the control module 102 to the paddle body 104. The paddle body 104 and the one or more lead bodies 106 form the lead 103. The paddle body 104 typically includes a plurality of electrodes 134 that form an array of electrodes 133. The control module 102 typically includes an electronic subassembly 110 and an optional power source 120 disposed in a sealed housing 114. In FIG. 1, two lead bodies 106 are shown coupled to the control module 102.

The control module 102 typically includes one or more connector assemblies 144 into which the proximal end of the one or more lead bodies 106 can be plugged to make an electrical connection via connector contacts (e.g., 316 in FIG. 3A) disposed in the connector assembly 144 and terminals (e.g., 310 in FIG. 3A) on each of the one or more lead bodies 106. The connector contacts are coupled to the electronic subassembly 110 and the terminals are coupled to the electrodes 134. In FIG. 1, two connector assemblies 144 are shown.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
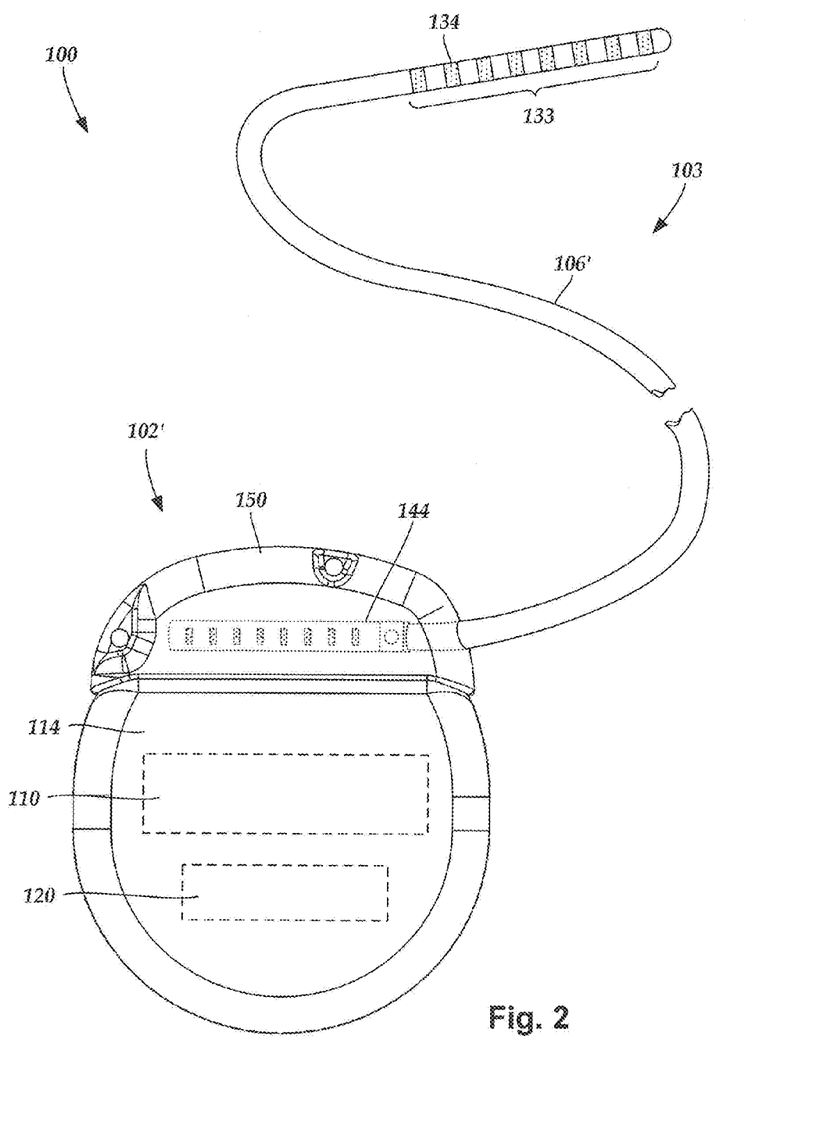
FIG. 2 is a schematic view of another embodiment of an electrical stimulation system that includes a percutaneous lead body coupled to a control module via a lead body, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of a lead body 106' forming a percutaneous lead 103, as illustrated in FIG. 2. The percutaneous lead may be isodiametric along the length of the lead body 106". The lead body 106' can be coupled with a control module 102' with a single connector assembly 144.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, muscle activation via stimulation of nerves innervating muscle, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 133 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead 103 to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A) are typically disposed at the proximal end of the one or more lead bodies 106 for connection to corresponding conductive contacts (e.g., 316 in FIG. 3A) in connector assemblies (e.g., 144 in FIG. 1) disposed on, for example, the control module 102 (or to other devices, such as conductive contacts on a lead extension, an operating room cable, a splitter, an adaptor, or the like).

Conductive wires (not shown) extend from the terminals (e.g., 310 in FIG. 3A) to the electrodes 134. Typically, one or more electrodes 134 are electrically coupled to a terminal (e.g., 310 in FIG. 3A). In some embodiments, each terminal (e.g., 310 in FIG. 3A) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. The one or more lumens may, optionally, be flushed continually, or on a regular basis, with saline, epidural fluid, or the like. The one or more lumens can be permanently or removably sealable at the distal end.

As discussed above, the one or more lead bodies 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1, each of the two lead bodies 106 includes eight terminals that are shown coupled with eight conductive contacts disposed in a different one of two different connector assemblies 144.

Figure 3A:
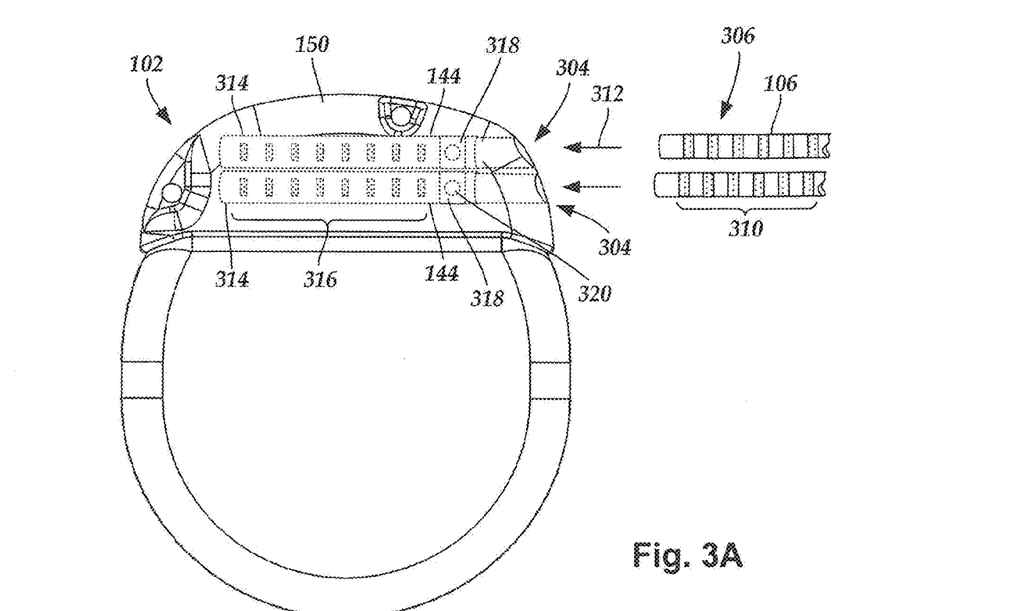
FIG. 3A is a schematic view of one embodiment of a plurality of connector assemblies disposed in the control module of FIG. 1, the connector assemblies configured and arranged to receive the proximal portions of the lead bodies of FIG. 1, according to the invention.
Figure 3B:
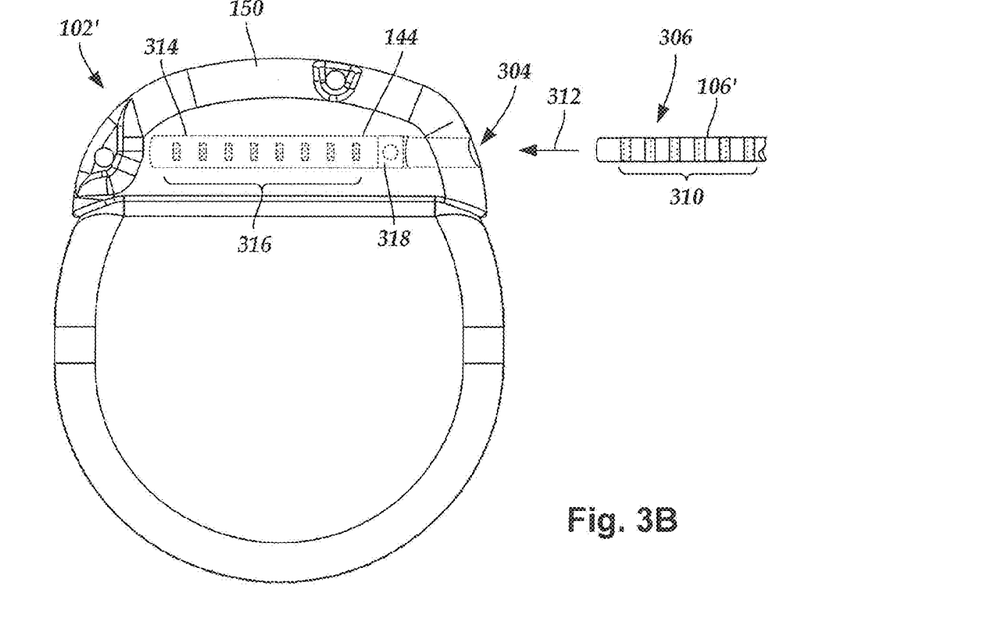
FIG. 3B is a schematic view of one embodiment of a connector assembly disposed in the control module of FIG. 2, the connector assembly configured and arranged to receive the proximal portion of one of the lead body of FIG. 2, according to the invention.

FIG. 3A is a schematic side view of one embodiment of a plurality of connector assemblies 144 disposed on the control module 102. In at least some embodiments, the control module 102 includes two connector assemblies 144. In at least some embodiments, the control module 102 includes four connector assemblies 144. In FIG. 3A, proximal ends 306 of the plurality of lead bodies 106 are shown configured and arranged for insertion to the control module 102. FIG. 3B is a schematic side view of one embodiment of a single connector assembly 144 disposed on the control module 102'. In FIG. 3B, the proximal end 306 of the single lead body 106' is shown configured and arranged for insertion to the control module 102'.

In FIGS. 3A and 3B, the one or more connector assemblies 144 are disposed in the header 150. In at least some embodiments, the header 150 defines one or more ports 304 into which the proximal end(s) 306 of the one or more lead bodies 106/106' with terminals 310 can be inserted, as shown by directional arrows 312, in order to gain access to the connector contacts disposed in the one or more connector assemblies 144.

The one or more connector assemblies 144 each include a connector housing 314 and a plurality of connector contacts 316 disposed therein. Typically, the connector housing 314 defines a port (not shown) that provides access to the plurality of connector contacts 316. In at least some embodiments, one or more of the connector assemblies 144 further includes a retaining element 318 configured and arranged to fasten the corresponding lead body 106/106' to the connector assembly 144 when the lead body 106/106' is inserted into the connector assembly 144 to prevent undesired detachment of the lead body 106/106' from the connector assembly 144. For example, the retaining element 318 may include an aperture 320 through which a fastener (e.g., a set screw, pin, or the like) may be inserted and secured against an inserted lead body 106/106'.

When the one or more lead bodies 106/106' are inserted into the one or more ports 304, the connector contacts 316 can be aligned with the terminals 310 disposed on the one or more lead bodies 106/106' to electrically couple the control module 102 to the electrodes (134 of FIG. 1) disposed at a distal end of the one or more lead bodies 106. Examples of connector assemblies in control modules are found in, for example, U.S. Pat. Nos. 7,244,150 and 8,224,450, which are incorporated by reference.

Figure 3C:
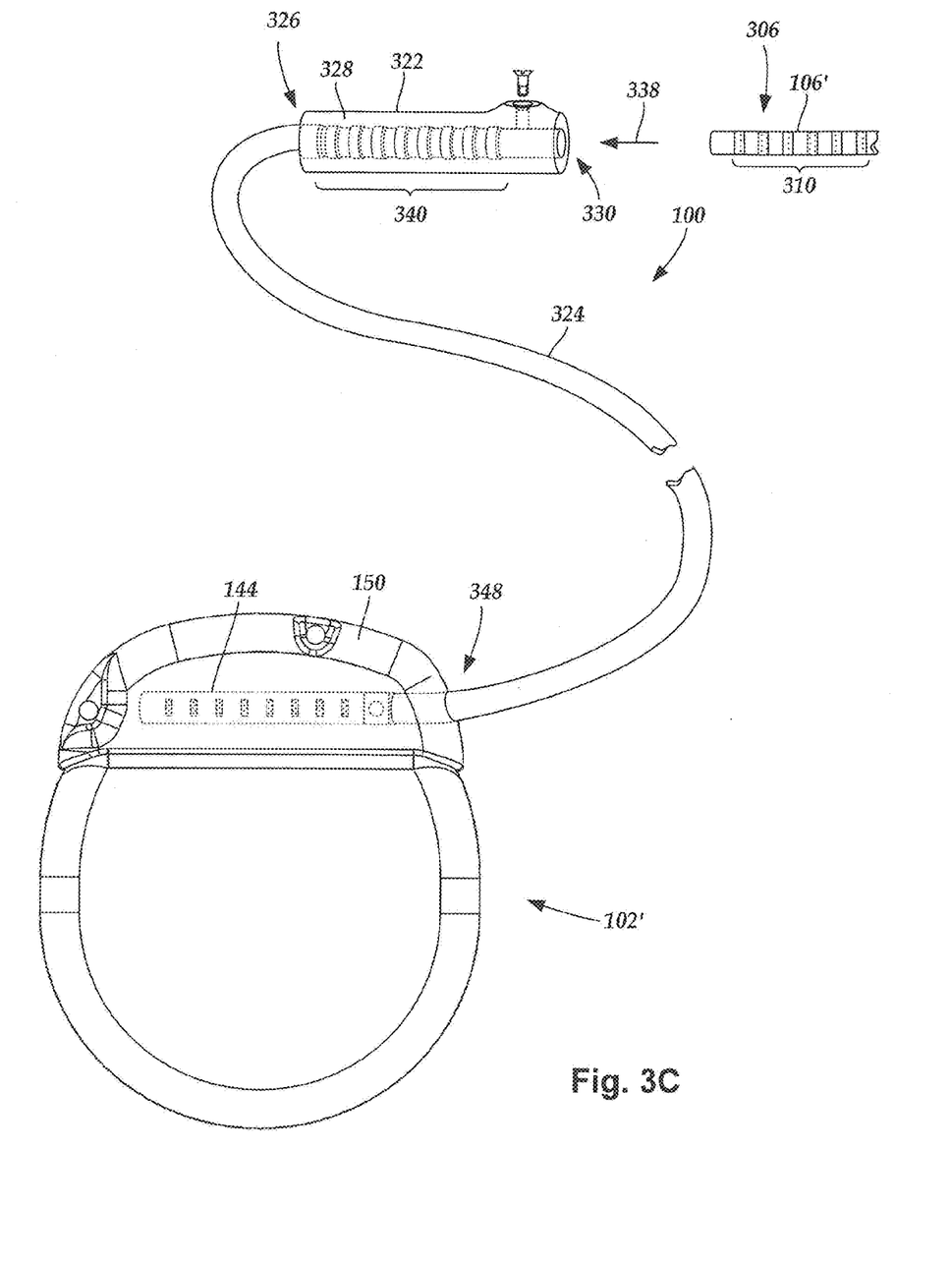
FIG. 3C is a schematic view of one embodiment of a proximal portion of the lead body of FIG. 2, a lead extension, and the control module of FIG. 2, the lead extension configured and arranged to couple the lead body to the control module, according to the invention.

In at least some embodiments, the electrical stimulation system includes one or more lead extensions. The one or more lead bodies 106/106' can be coupled to one or more lead extensions which, in turn, are coupled to the control module 102/102'. In FIG. 3C, a lead extension connector assembly 322 is disposed on a lead extension 324. The lead extension connector assembly 322 is shown disposed at a distal end 326 of the lead extension 324. The lead extension connector assembly 322 includes a contact housing 328. The contact housing 328 defines at least one port 330 into which a proximal end 306 of the lead body 106' with terminals 310 can be inserted, as shown by directional arrow 338. The lead extension connector assembly 322 also includes a plurality of connector contacts 340. When the lead body 106' is inserted into the port 330, the connector contacts 340 disposed in the contact housing 328 can be aligned with the terminals 310 on the lead body 106 to electrically couple the lead extension 324 to the electrodes (134 of FIG. 1) disposed at a distal end (not shown) of the lead body 106'.

The proximal end of a lead extension can be similarly configured and arranged as a proximal end of a lead body. The lead extension 324 may include a plurality of conductive wires (not shown) that electrically couple the connector contacts 340 to terminal on a proximal end 348 of the lead extension 324. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a lead extension connector assembly disposed in another lead extension. In other embodiments (as shown in FIG. 3C), the proximal end 348 of the lead extension 324 is configured and arranged for insertion into the connector assembly 144 disposed on the control module 102'.

It will be understood that the control modules 102/102' can receive either lead bodies 106/106' or lead extensions 324. It will also be understood that the electrical stimulation system 100 can include a plurality of lead extensions 224. For example, each of the lead bodies 106 shown in FIGS. 1 and 3A can, alternatively, be coupled to a different lead extension 224 which, in turn, are each coupled to different ports of a two-port control module, such as the control module 102 of FIGS. 1 and 3A.

Figure 4A:
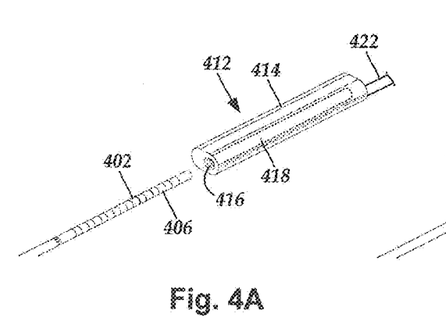
FIG. 4A is a schematic perspective view of one embodiment of a proximal end of a lead and a connector assembly configured to receive the proximal end of the lead, according to the invention.

Turning to FIG. 4A, some patients may find that implanted connector assemblies cause pain and discomfort, and in some cases, may also cause skin erosion in or around the area of implantation. Such conditions may be attributable, at least in part, to the size and shape of the connector assemblies.

Additionally, some patients may find that when, for example, the patient applies tension to the region of implantation, or when the patient engages in a jerking motion, a temporarily misalignment may occur between the connector assembly and the lead or lead extension coupled to the connector assembly. The misalignment may be attributable to the flexibility along a longitudinal length of the connector assembly. Misalignment may cause electrical mis-registration between the connector contacts of the connector assembly and the terminals of the lead or lead extension inserted into the connector assembly. In some cases, mis-registration can ultimately result in failure of the electrical stimulation system.

At least some conventional connector assemblies use connector contacts formed from coiled springs adapted to completely encircle terminals when making electrical connection with the terminals. The use of coiled springs for connector contacts may contribute to an increase in diameter in all directions along a longitudinal length of the connector assemblies due to the complete encirclement of the terminals by the coiled springs.

As herein described, an improved connector assembly may be used with implantable medical devices, such as electrical stimulation systems. The improved connector assembly can have a reduced width from conventional connectors along at least one axis transverse to a longitudinal axis of the connector assembly. In at least some embodiments, the improved connector assembly maintains a constant shape along the entire longitudinal axis of the connector assembly. In at least some embodiments, the improved connector assembly maintains a constant size along the entire longitudinal axis of the connector assembly. In at least some embodiments, the improved connector assembly has a decreased potential for misalignment from conventional connector assemblies between the lead or lead extension and the connector assembly.

The improved connector assembly includes connector contacts formed as spring contact probes. In at least some embodiments, the spring contact probes are configured and arranged to physically contact terminals of an inserted lead or lead extension along a single axis transverse to a longitudinal axis of the connector assembly, thereby enabling the connector assembly to have reduced diameters along other axes transverse to the longitudinal axis. In at least some embodiments, the spring contact probes are coupled to a support element that extends along the longitudinal axis of the connector assembly. In which case, the support element provides stiffness to the connector assembly that may reduce the flexibility along the longitudinal length of the connector assembly, thereby reducing the potential for misalignment between the connector contacts and the terminals of inserted leads or lead extensions.

FIG. 4A is a schematic perspective view of one embodiment of a proximal end of a lead 402 and a connector assembly 412 configured to receive the proximal end of the lead 402. The lead 402 includes a plurality of terminals, such as terminal 406. The connector assembly 412 includes a housing 414 that defines a port 416. The housing 414 also defines a lumen 418 that opens at the port 416. The port 416 and the lumen 418 are both configured and arranged to receive the proximal end of the lead 402.

Figure 4B:
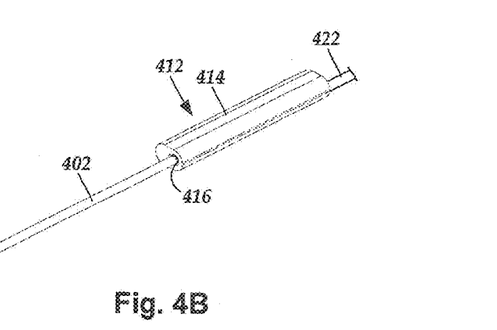
FIG. 4B is a schematic perspective view of one embodiment of the proximal end of the lead of FIG. 4A received by the connector assembly of FIG. 4A, according to the invention.

FIG. 4B is a schematic perspective view of one embodiment of the proximal end of the lead 402 coupled to the connector assembly 412. In FIG. 4B, the proximal end of the lead 402 is shown inserted into the port 416 and the lumen 418 of the connector assembly 412. In FIGS. 4A-4B (and in other figures), the connector assembly 412 is shown disposed on a distal end of a lead extension 422. It will be understood that connector assemblies can be disposed in many different locations including, for example, lead extensions, lead adapters, lead splitters, control modules (see e.g., 144 of FIGS. 1-3B), or the like. In at least some embodiments, the connector assembly can be disposed along the proximal end of the lead.

Figures 5A, 5B:
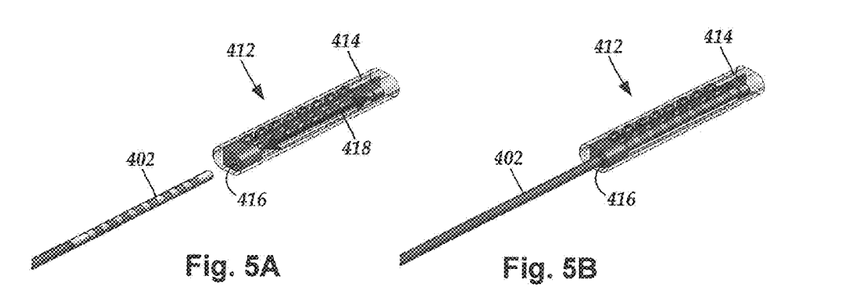
FIG. 5A is a schematic perspective view of one embodiment of a proximal end of the lead of FIG. 4A and the connector assembly of FIG. 4A, the connector assembly having a transparent housing through which at least some of the inner components of connector assembly are visible, according to the invention.
FIG. 5B is a schematic perspective view of one embodiment of the proximal end of the lead of FIG. 4A received by the connector assembly of FIG. 4A, the connector assembly having a transparent housing through which the proximal end of the lead is visible within the connector assembly, according to the invention.

FIG. 5A is a schematic perspective view of one embodiment of the proximal end of the lead 402 and the connector assembly 412, where the connector assembly 412 is configured to receive the lead 402. FIG. 5B is a schematic perspective view of one embodiment of the proximal end of the lead 402 inserted into the port 416 of the connector assembly 412.

In FIGS. 5A-5B, the housing 414 is illustrated as transparent so that some of the components disposed in the interior of the connector assembly 412 are visible through the housing 414. In FIG. 5A, the lumen 418 is shown by a two-headed arrow. In FIG. 5B, the proximal end of the lead 402 is shown within the connector assembly 412. As shown in FIG. 5B, the lead 402 is inserted into the port 416 such that the lead 402 extends within the connector assembly 412 along the lumen 418.

Figure 6:
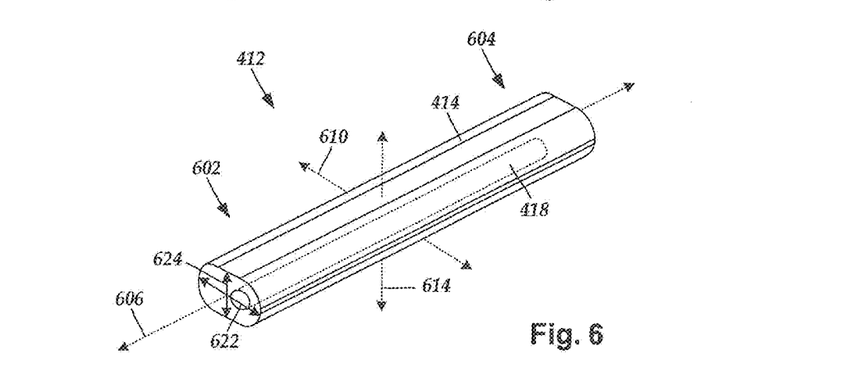
FIG. 6 is a schematic perspective view of one embodiment of the connector assembly of FIG. 4A, according to the invention.

FIG. 6 is a schematic perspective view of one embodiment of the connector assembly 412. The connector housing 414 of the connector assembly 412 has a first end 602, an opposing second end 604, and a longitudinal axis 606 extending between the first end 602 and the second end 604. In at least some embodiments, the lumen 418 extends parallel with the longitudinal axis 606 of the connector housing 414. The connector housing 414 has a first transverse axis 610 that is transverse to the longitudinal axis 606. The connector housing 414 also has a second transverse axis 614 that is transverse to the longitudinal axis 606 and perpendicular to the first transverse axis 610.

The connector housing 414 has a first width 622 along the first transverse axis 610 and a second width 624 along the second transverse axis 614. In at least some embodiments, the first width 622 is constant along the entire longitudinal axis 606 of the connector housing 414. In at least some embodiments, the second width 624 is constant along the entire longitudinal axis 606 of the connector housing 414.

In at least some embodiments, the first width 622 is larger than the second width 624. In at least some embodiments, the first width 622 is larger than the second width 624 by at least 5%, 10%, 15%, 20%, 25%, 30%, 40%, 50%, or more. In at least some embodiments, the second width 624 is no greater than 0.25 inches (approximately 0.6 cm), 0.23 inches (approximately 0.6 cm), 0.21 inches (approximately 0.5 cm), 0.19 inches (approximately 0.5 cm), 0.17 inches (approximately 0.4 cm), or 0.15 inches (approximately 0.6 cm).

The above-described embodiments of the connector assembly have volumetric profiles that are significantly smaller than other conventional connector assemblies along at least one axis (e.g., along the second transverse axis 614). It may be advantageous to reduce the dimensions of a connector assembly to potentially increase the number of implantation locations, and also to potentially decrease patient discomfort during implantation and operation of the connector assembly.

Figure 7A:
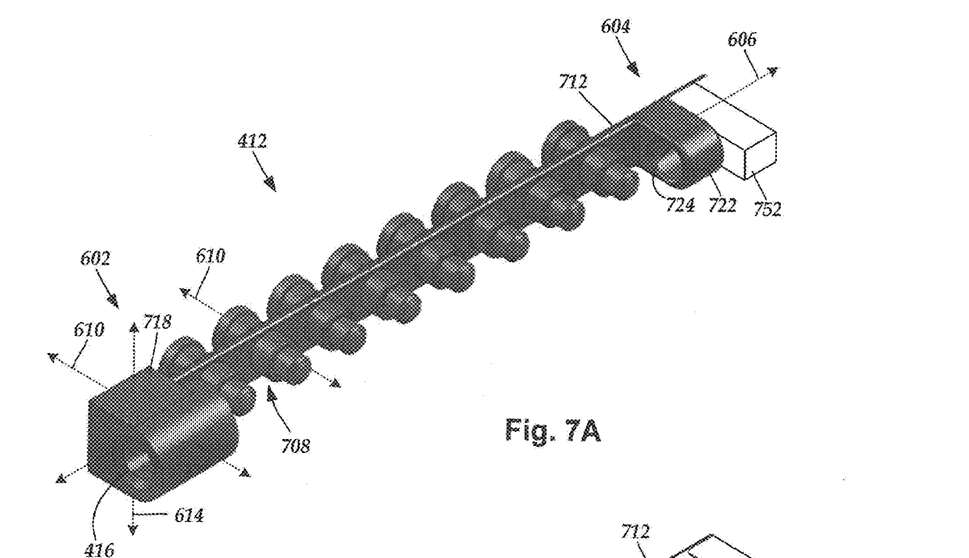
FIG. 7A is a schematic perspective view of one embodiment of the connector assembly of FIG. 4A with the housing removed, the connector assembly including a plurality of connector contacts, according to the invention.
Figure 7B:
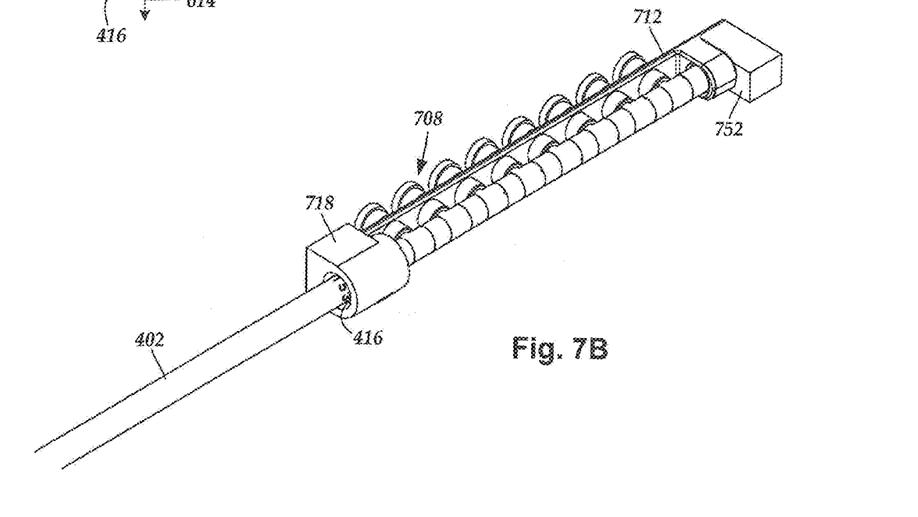
FIG. 7B is a schematic perspective view of one embodiment of the lead of FIG. 4A coupled to the housing-less connector assembly of FIG. 7A such that terminals of the lead couple with connector contacts of the connector assembly, according to the invention.

FIG. 7A is a schematic perspective view of one embodiment of the connector assembly 412 with the connector housing 414 removed. The connector assembly 412 includes a plurality of connector contacts, such as connector contact 708. FIG. 7B is a schematic perspective view of one embodiment of a proximal end of the lead 402 coupled to the connector assembly 412 such that the terminals 406 of the lead 402 couple with the connector contacts 708 of the connector assembly 412. In at least some embodiments, each of the connector contacts 708 is oriented in the same direction.

Optionally, a retaining element 718 is disposed along the first end 602 of the connector assembly 412. The retaining element 718 is configured and arranged to fasten the lead 402 to the connector assembly 412 when the lead 402 is inserted into the connector assembly 412 to prevent undesired detachment of the lead 402 from the connector assembly 412. For example, the retaining element 718 may include an aperture (see e.g., aperture 320 in FIG. 3A) through which a fastener (e.g., a set screw, pin, or the like) may be inserted and secured against the inserted lead 402. In at least some embodiments, the aperture extends along the first transverse axis 610.

Optionally, an end stop 722 is disposed along the second end 604 of the connector assembly 412 and is in communication with the lumen 418. The end stop 722 is configured and arranged to modulate insertion of the lead 402 into the connector assembly 412. The end stop 722 provides at least one surface 724 that contacts the lead 402 when the lead 402 is fully inserted into the lumen 418 of the connector assembly 412 and prevents further insertion of the lead 402. In at least some embodiments, the connector assembly 412 is configured and arranged such that, when the lead 402 is fully inserted into the connector assembly 412 with the lead 402 contacting the end stop 722, the terminals 406 of the lead 402 are aligned with, and in electrical contact with, the connector contacts 708.

The connector assembly 412 may include one or more support elements 712 extending along the longitudinal axis 606 of the connector housing 414. In at least some embodiments, the one or more support elements 712 provide support for the connector contacts 708. The one or more support elements 712 can be formed as one or more plates, rods, bars, or the like or combinations thereof. The one or more support elements 712 can be formed from any suitable material with sufficient rigidity to reduce the potential for mis-registration including, for example, plastic, metal (e.g., titanium, MP35N, or the like). In at least some embodiments, the one or more support elements 712 are formed completely from non-conductive material(s). In at least some embodiments, the one or more support elements 712 include an electrically-insulated outer layer.

In at least some embodiments, the spring contact probes 708 are mechanically coupled (e.g., welded, bonded, or the like) to the one or more support elements 712. In at least some embodiments, the retaining element 718 is mechanically coupled (e.g., welded, bonded, or the like) to the one or more support elements 712. In at least some embodiments, the end stop 722 is mechanically coupled (e.g., welded, bonded, or the like) to the one or more support elements 712.

Referring briefly back to FIGS. 4A-5B, the connector assembly 412 is shown defining the lumen 418 along which the lead 402 extends when the lead 402 is inserted into the connector assembly 412. As shown in FIGS. 7A-7B, in at least some embodiments a portion of the lumen 418 is formed by the retaining element 718. As also shown in FIGS. 7A-7B, in at least some embodiments a portion of the lumen 418 is formed by the end stop 722.

Figure 8A:
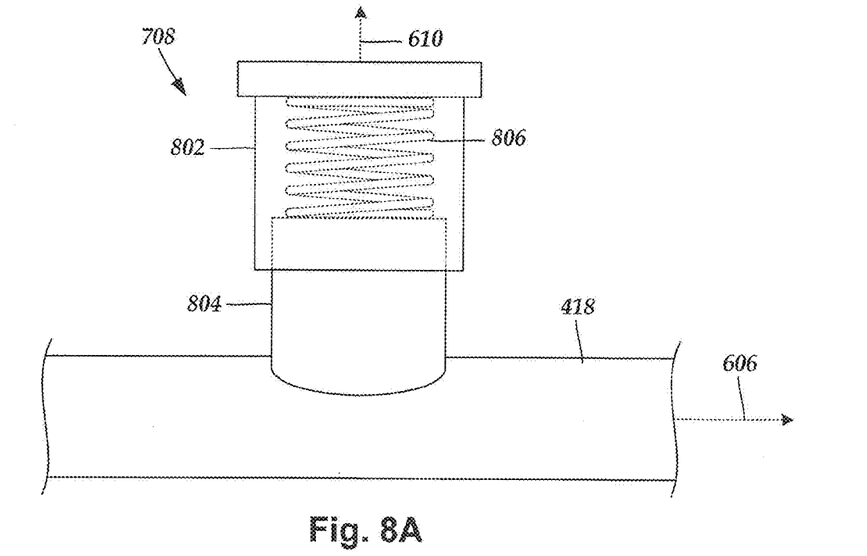
FIG. 8A is a schematic side view of one embodiment of a connector contact of the plurality of connector contacts of FIG. 7A extending partially into a lumen of the connector assembly of FIG. 4A, the connector contact including a biasing element in a relaxed position, according to the invention.
Figure 8B:
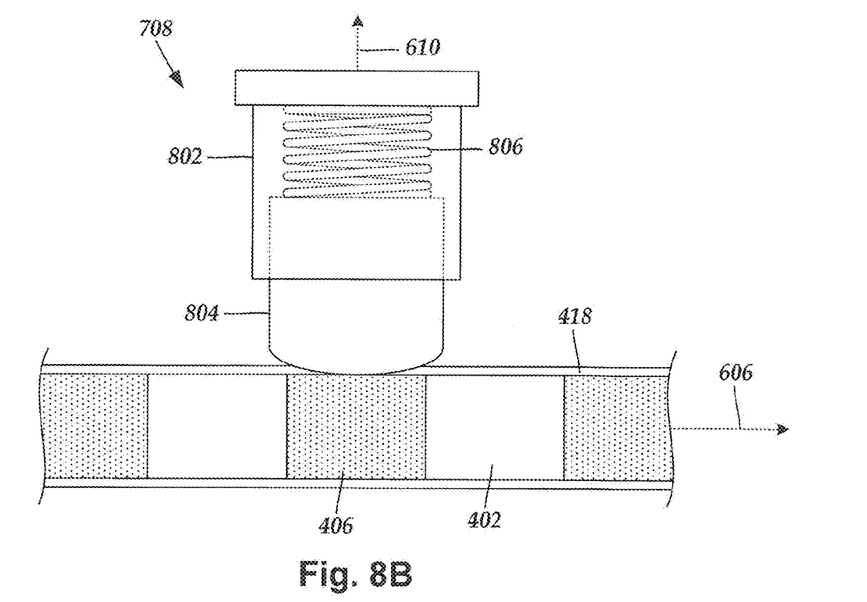
FIG. 8B is a schematic side view of one embodiment of the connector contact of FIG. 8A physically contacting a terminal of the lead of FIG. 4A inserted into a lumen of the connector assembly of FIG. 4A, the connector contact including a biasing element in a compressed position, according to the invention.

Turning to FIGS. 8A-8B, in at least some embodiments the connector contacts 708 are formed as spring contact probes. FIG. 8A is a schematic side view of one embodiment of the connector contact 708 extending partially into the lumen 418. FIG. 8B is a schematic side view of one embodiment of the connector contact 708 extending partially into the lumen 418 and physically contacting one of the plurality of terminals 406 of the lead 402 extending along the lumen 418.

The spring contact probes 708 each include a contact housing 802 and a spring-loaded pin 804 that is formed from a conductive material and that is configured and arranged to couple with a terminal (e.g., of the lead 402, or a lead extension, or the like). The spring contact probes 708 can be formed, either completely or in part (e.g., coated), using any conductive material suitable for implantation including, for example, Nitinol, stainless steel (e.g., 316L, or the like), platinum iridium, or the like.

In at least some embodiments, the spring-loaded pin 804 is electrically coupled to one or more elongated conductors (not shown) that electrically couple the spring contact probes 708 to an electronic device (e.g., the electronic subassembly 110 in FIG. 1) such that, when the spring-loaded pin 804 is coupled to the terminal 406 the electronic device is coupled to the electrodes (see e.g., 134 in FIG. 1). When the spring-loaded pin 804 is electrically coupled to one or more elongated conductors, the elongated conductors can be directly coupled to the spring-loaded pin 804, or the elongated conductors can be coupled to the spring-loaded pin 804 via one or more of the contact housing 802, the one or more support elements 712, or the biasing element 806 (described below).

In at least some embodiments, a biasing element (e.g., one or more coiled springs, one or more leaf springs, one or more elastomeric materials, or the like) 806 is disposed in the contact housing 802 and is coupled to the spring-loaded pin 804. The biasing element 806 is configured and arranged to compress or expand between a relaxed position (see e.g., FIG. 8A) and a compressed position (see e.g., FIG. 8B). The biasing element 806 is coupled to the spring-loaded pin 804 such that compression or expansion of the biasing element 806 causes a corresponding movement of the spring-loaded pin 804 along an axis (e.g., the first transverse axis 610). As shown in FIG. 8A, when the spring contact probe 708 is in a relaxed position, at least a portion of the spring-loaded pin 804 extends at least partially into the lumen 418.

Each of the spring-loaded pins 804 extends from one end of its corresponding contact housing 802. In at least some embodiments, each of the contact housings 802 has a length that is parallel to the first transverse axis 610. In at least some embodiments, each of the spring-loaded pins 804 extends from one end of its corresponding contact housing 802 along the first transverse axis 610.

As shown in FIG. 8B, when the spring-loaded pins 804 are aligned along the first transverse axis 610, the spring-loaded pins 804 are configured and arranged such that at least a portion of the spring-loaded pins 804 retract into the contact housing 802 upon application of a force against the spring-loaded pins 804 along the first transverse axis 610 generally in the direction of the retraction. While retracted, the spring-loaded pins 804 continuously apply a force in the direction opposite to the direction of retraction along the first transverse axis 610. Thus, when the force applied to the spring-loaded pins 804 is removed, the retracted spring-loaded pins 804 return to their relaxed position with at least a portion of the spring-loaded pins 804 extending at least partially into the lumen 418.

When, as shown in FIG. 8B, the lead 402 is inserted into the connector assembly 412, the lead 402 exerts a force on the spring-loaded pins 804 that causes the spring-loaded pins 804 to retract. While retracted, the spring-loaded pins 804 continuously apply a force against the surface of the inserted lead 402, thereby maintaining mechanical contact with the lead 402. In at least some embodiments, when the lead 402 is operationally inserted into the connector assembly 412, the spring-loaded pins 804 align with the terminals 406 of the lead 402. In which case, the force applied against the terminals 406 by the refracted spring-loaded pins 804 forms (and maintains) an electrical connection between the connector assembly 412 and the inserted lead 402. In at least some embodiments, the spring-loaded pins 804 are configured and arranged to physically contact the terminals 406 solely along the first transverse axis 610.

Referring back to FIGS. 7A-7B, the spring contact probes 708 can, optionally, incorporate an actuator (e.g., a button, a lever, or the like) 752 to control how far the spring-loaded pins 804 extend into the lumen 418 of the connector assembly 412 when the spring-loaded pins 804 are in a relaxed position. In at least some embodiment, the actuator 752 can be actuated, either manually or automatically, to pull the spring-loaded pins 804 away from the lumen 418 prior to insertion of the lead 402. Pulling the spring-loaded pins 804 away from the lumen 418 may reduce friction and insertion forces during the insertion of the lead 402 into the lumen 418. In at least some embodiments, the actuator 752 automatically returns the spring-loaded pins 804 to their relaxed position after a set amount of time. In at least some other embodiments, the spring-loaded pins 804 are returned to their relaxed positions upon re-actuation of the actuator 752.

The above-described embodiments of the connector assembly are significantly stiffer than other conventional connector assemblies along the longitudinal axis. It may be advantageous to increase to stiffness of the connector assembly along the longitudinal axis to potentially reduce mis-alignments and mis-registrations between the components being connected.

The above-described embodiments of the connector assembly are suitable for use with a variety of different connectors of electrical stimulation systems (e.g., lead extension connectors, control module connectors, or the like). The above-described embodiments of the connector assembly are suitable for use with a variety of different electrical stimulation systems (e.g., spinal cord stimulation systems, deep brain stimulation systems, or the like). The above-described embodiments of the connector assembly are also suitable for use with a variety of different connector systems of a variety of different implantable medical devices.

Figure 9:
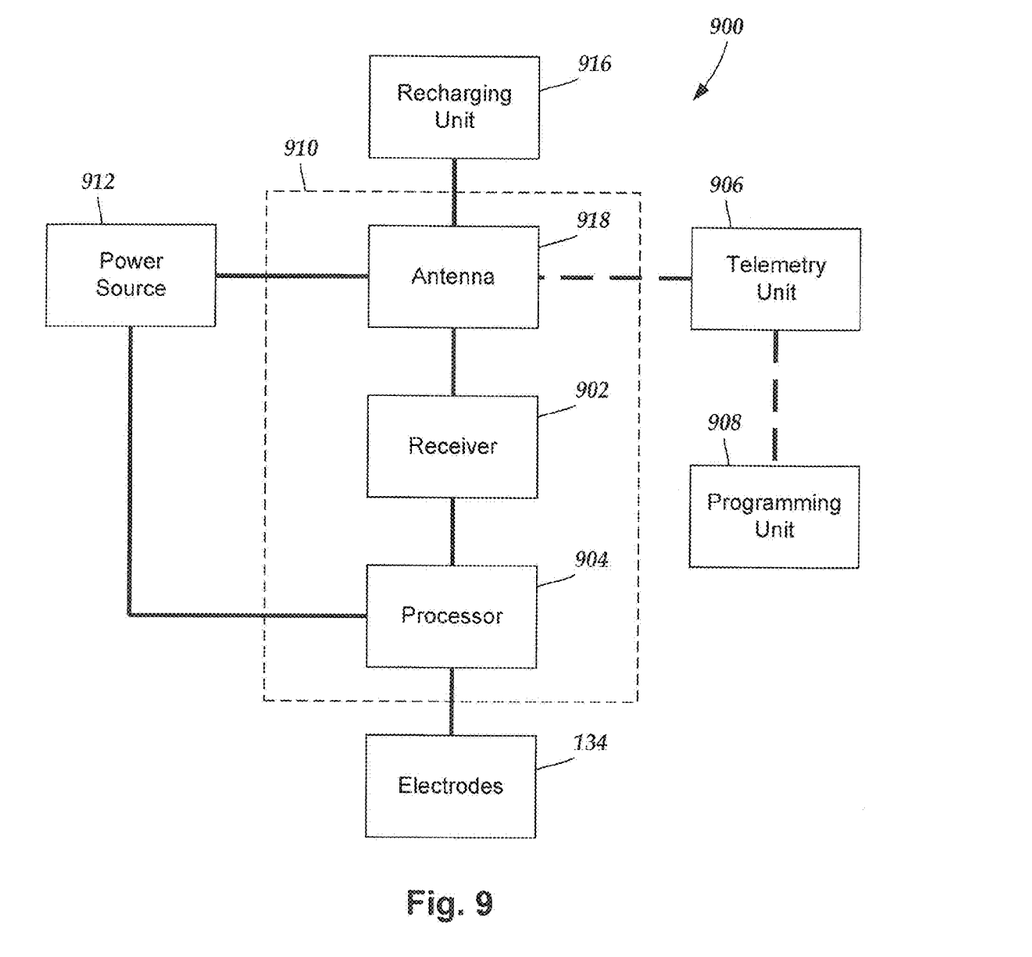
FIG. 9 is a schematic overview of one embodiment of components of an electrical stimulation system, according to the invention.

FIG. 9 is a schematic overview of one embodiment of components of an electrical stimulation system 900 including an electronic subassembly 910 disposed within a control module. It will be understood that the electrical stimulation system can include more, fewer, or different components and can have a variety of different configurations including those configurations disclosed in the stimulator references cited herein.

Some of the components (for example, power source 912, antenna 918, receiver 902, and processor 904) of the electrical stimulation system can be positioned on one or more circuit boards or similar carriers within a sealed housing of an implantable pulse generator, if desired. Any power source 912 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 918 or a secondary antenna. The external power source can be in a device that is mounted on the skin of the user or in a unit that is provided near the user on a permanent or periodic basis.

If the power source 912 is a rechargeable battery, the battery may be recharged using the optional antenna 918, if desired. Power can be provided to the battery for recharging by inductively coupling the battery through the antenna to a recharging unit 916 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 904 is generally included to control the timing and electrical characteristics of the electrical stimulation system. For example, the processor 904 can, if desired, control one or more of the timing, frequency, strength, duration, and waveform of the pulses. In addition, the processor 904 can select which electrodes can be used to provide stimulation, if desired. In some embodiments, the processor 904 may select which electrode(s) are cathodes and which electrode(s) are anodes. In some embodiments, the processor 904 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 908 that, for example, allows modification of pulse characteristics. In the illustrated embodiment, the processor 904 is coupled to a receiver 902 which, in turn, is coupled to the optional antenna 918. This allows the processor 904 to receive instructions from an external source to, for example, direct the pulse characteristics and the selection of electrodes, if desired.

In one embodiment, the antenna 918 is capable of receiving signals (e.g., RF signals) from an external telemetry unit 906 which is programmed by a programming unit 908. The programming unit 908 can be external to, or part of, the telemetry unit 906. The telemetry unit 906 can be a device that is worn on the skin of the user or can be carried by the user and can have a form similar to a pager, cellular phone, or remote control, if desired. As another alternative, the telemetry unit 906 may not be worn or carried by the user but may only be available at a home station or at a clinician's office. The programming unit 908 can be any unit that can provide information to the telemetry unit 906 for transmission to the electrical stimulation system 900. The programming unit 908 can be part of the telemetry unit 906 or can provide signals or information to the telemetry unit 906 via a wireless or wired connection. One example of a suitable programming unit is a computer operated by the user or clinician to send signals to the telemetry unit 906.

The signals sent to the processor 904 via the antenna 918 and receiver 902 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 900 to cease operation, to start operation, to start charging the battery, or to stop charging the battery. In other embodiments, the stimulation system does not include an antenna 918 or receiver 902 and the processor 904 operates as programmed.

Optionally, the electrical stimulation system 900 may include a transmitter (not shown) coupled to the processor 904 and the antenna 918 for transmitting signals back to the telemetry unit 906 or another unit capable of receiving the signals. For example, the electrical stimulation system 900 may transmit signals indicating whether the electrical stimulation system 900 is operating properly or not or indicating when the battery needs to be charged or the level of charge remaining in the battery. The processor 904 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead extension comprising:
   a lead-extension body with a proximal end, a distal end, and a longitudinal length;
   a plurality of terminals disposed on the proximal end of the lead-extension body;
   a connector assembly disposed along the distal end of the lead-extension body, the connector housing comprising
      an elongated connector housing having a first end, an opposing second end, a longitudinal axis, a first transverse axis transverse to the longitudinal axis, and a second transverse axis transverse to the longitudinal axis and perpendicular to the first transverse axis,
      a port defined at the first end of the connector housing, the port configured and arranged for receiving a proximal end of a lead,
      a lumen defined in the connector housing, the lumen extending from the port along the longitudinal axis of the connector housing, and
      a plurality of connector contacts disposed in the connector housing, at least one of the plurality of connector contacts configured and arranged to couple to at least one of a plurality of lead terminals disposed on the proximal end of the lead when the proximal end of the lead is received by the connector housing; and
   a plurality of lead-extension conductors, each lead-extension conductor electrically coupling at least one of the plurality of connector contacts to at least one of the lead-extension terminals;
   wherein the plurality of connector contacts comprise a plurality of spring contact probes spaced apart from one another along the longitudinal axis of the connector housing with at least a portion of each of the plurality of spring contact probes extending along the first transverse axis into the lumen of the connector housing;
   wherein the plurality of spring contact probes are configured and arranged to physically contact the lead terminals solely along the first transverse axis when the proximal end of the lead is received by the connector housing.

2. The lead extension of claim 1, wherein each of the plurality of spring contact probes comprises
   a contact housing having a first end and an opposing second end,
   a biasing element disposed in the connector housing, the biasing element configured and arranged to transition between a relaxed position and a compressed position, and
   an electrically-conductive spring-loaded pin coupled to the biasing element and extending from the first end of the contact housing along the first transverse axis, wherein transitioning by the biasing element causes a corresponding movement of the spring-loaded pin along the first transverse axis of the contact housing;
   wherein the spring-loaded pin extends at least partially into the lumen of the connector assembly and is configured and arranged to couple to at least one of a plurality of lead terminals when the proximal end of the lead is received by the connector housing.

3. The lead extension of claim 2, further comprising an actuator for facilitating transitioning of the biasing element between the relaxed position and the compressed position.

4. The lead extension of claim 3, wherein the actuator comprises at least one of a button or a lever.

5. The lead extension of claim 1, further comprising at least one elongated support element disposed along the longitudinal axis of the connector housing.

6. The lead extension of claim 5, wherein each of the plurality of spring contact probes is coupled to the at least one support element.

7. The lead extension of claim 1, wherein the connector assembly further comprises a retaining element disposed along the first end of the connector housing, the retaining element configured and arranged for retaining a proximal end of the lead when the proximal end of the lead is inserted into the lumen.

8. The lead extension of claim 7, wherein the retaining element defines an aperture extending along the first transverse axis.

9. The lead extension of claim 7, wherein the retaining element is coupled to at least one support element disposed along the longitudinal axis of the connector housing.

10. The lead extension of claim 1, further comprising an end stop disposed along the second end of the connector housing, the end stop configured and arranged for modulating insertion of the lead into the lumen of the connector assembly.

11. The lead extension of claim 10, wherein the end stop is coupled to at least one support element disposed along the longitudinal axis of the connector housing.

12. The lead extension of claim 10, wherein the connector housing has a first width along the first transverse axis and a second width along the second transverse axis, and wherein the first width is larger than the second width.

13. The lead extension of claim 12, wherein the first width is constant along the entire longitudinal axis.

14. The lead extension of claim 12, wherein the second width is constant along the entire longitudinal axis.

15. The lead extension of claim 12, wherein the first width is larger than the second width by at least 10%.

16. The lead extension of claim 12, wherein the second width is no greater than 0.15 inches.

17. A lead assembly comprising:
    a lead comprising
       a lead body with a proximal end, a distal end, and a longitudinal length,
       a plurality of electrodes disposed on the distal end of the lead body,
       a plurality of lead terminals disposed on the proximal end of the lead body, and
       a plurality of conductors electrically coupling the plurality of electrodes to the plurality of lead terminals; and
    the lead extension of claim 12;
    wherein the proximal end of the lead is configured and arranged for insertion into the port and the lumen of the connector assembly of the lead extension.

18. An electrical stimulating system comprising:
the lead assembly of claim 17; and
a control module electrically coupled to the plurality of electrodes of the lead of the lead assembly, the control module comprising
 a housing, and
 an electronic subassembly disposed in the housing;
wherein the proximal end of the lead extension is configured and arranged for coupling with the control module.

19. A lead assembly comprising:
a lead comprising
 a lead body with a proximal end, a distal end, and a longitudinal length,
 a plurality of electrodes disposed on the distal end of the lead body,
 a plurality of lead terminals disposed on the proximal end of the lead body, and
 a plurality of conductors, each conductor electrically coupling at least one of the electrodes to at least one of the lead terminals; and
lead extension of claim 1;
wherein the proximal end of the lead is configured and arranged for insertion into the port and the lumen of the connector assembly of the lead extension.

20. An electrical stimulating system comprising:
the lead assembly of claim 19; and
a control module electrically coupled to the plurality of electrodes of the lead of the lead assembly, the control module comprising
 a housing, and
 an electronic subassembly disposed in the housing;
wherein the proximal end of the lead extension is configured and arranged for coupling with the control module.

* * * * *